US011761948B2

(12) United States Patent
Funk et al.

(10) Patent No.: US 11,761,948 B2
(45) Date of Patent: *Sep. 19, 2023

(54) TREATED DRIED BLOOD SAMPLE PAPER FOR DETECTION OF HEAVY METALS IN DRIED BLOOD

(71) Applicant: Northwestern University, Evanston, IL (US)

(72) Inventors: William E Funk, Evanston, IL (US); Thomas McDade, Evanston, IL (US)

(73) Assignee: Northwestern University, Evanston, IL (US)

( * ) Notice: Subject to any disclaimer, the term of this patent is extended or adjusted under 35 U.S.C. 154(b) by 403 days.

This patent is subject to a terminal disclaimer.

(21) Appl. No.: 14/778,234

(22) PCT Filed: Mar. 14, 2014

(86) PCT No.: PCT/US2014/028146
§ 371 (c)(1),
(2) Date: Sep. 18, 2015

(87) PCT Pub. No.: WO2014/152894
PCT Pub. Date: Sep. 25, 2014

(65) Prior Publication Data
US 2016/0245792 A1    Aug. 25, 2016

Related U.S. Application Data

(60) Provisional application No. 61/803,674, filed on Mar. 20, 2013.

(51) Int. Cl.
| | | |
|---|---|---|
| *A61B 5/15* | (2006.01) | |
| *G01N 33/49* | (2006.01) | |
| *A61B 5/145* | (2006.01) | |
| *G01N 33/84* | (2006.01) | |
| *A61B 5/151* | (2006.01) | |

(52) U.S. Cl.
CPC ......... *G01N 33/49* (2013.01); *A61B 5/14546* (2013.01); *A61B 5/150022* (2013.01); *A61B 5/15142* (2013.01); *A61B 5/150305* (2013.01); *A61B 5/150358* (2013.01); *A61B 5/150755* (2013.01); *G01N 33/84* (2013.01); *A61B 2562/0295* (2013.01); *A61B 2562/242* (2013.01)

(58) Field of Classification Search
CPC .............. G01N 33/49; A61B 5/150755; A61B 5/150858; A61B 5/150022
See application file for complete search history.

(56) References Cited

U.S. PATENT DOCUMENTS

| | | |
|---|---|---|
| 3,443,903 A | 5/1969 | Haack |
| 4,771,631 A | 9/1988 | Lehtikoski |
| 5,427,953 A | 6/1995 | Yee |
| 7,407,578 B2 | 8/2008 | Sakaino |
| 7,569,184 B2 | 8/2009 | Wandell |
| 7,926,661 B2 | 4/2011 | Beeman |

FOREIGN PATENT DOCUMENTS

GB    1073181    6/1967

OTHER PUBLICATIONS

Anonymous. Taking Blood From Infants for the HIV PCR Test; (2011) downloaded from http://www.nhls.ac.za/assets/files/3458%20Roche%20DBS%20Booklet%20LR.pdf on Jun. 13, 2017.*
Anonymous. Whatman: Touching Lives; Product Guide 2010-2011, downloaded from Http://www.laboplus.pl/images/stories/katalogi/2010_whatman_catalog_full_fnl.pdf on Sep. 18, 2017.*
Stove et al. Dried Blood Spots in Toxicology: From the Cradle to the Grave; Critical Reviews in Toxicology, vol. 42, No. 3 pp. 23-243. (Year: 2012).*
Anonymous. The Seven Strong Acids, downloaded from https://web.archive.org/web/20031027165745/http://www.cm.utexas.edu/academic/courses/Spring2002/CH301/McDevitt/strong.htm (Year: 2003).*
Anonymous, What is Deionized Water?, downloaded from https://puretecwater.com/deionized-water/what-is-deionized-water (Year: 2012).*
Lee et al. Estimation of Metal Impurities in High-Purity Nitric Acids Used for Metal Analysis By Inductively Coupled Plasma-Mass Spectrometry; Analytical Sciences, vol. 19, pp. 1561-1563. (Year: 2003).*
Anonymous, CHMlab. Ashless Hardened Filter Paper for Quantitative Analysis; downloaded from http://www.chmlab.com/en/Filtration/Quantitative-Filter-Paper/Ashless-hardened-filter-paper-for-quantitative-analysis/ (Year: 2005).*
Anonymous. Advantec Specialty Products, pp. 31-46. Downloaded from https://web.archive.org/web/20091116173315/http://www.advantecmfs.com/catalog/filt/specialty.pdf on Oct. 29, 2018. (Year: 2009).*
Langer et al. Characterization of the Elemental Composition of Newborn Blood Spots Using Sector-Field Inductively Coupled Plasma-Mass Spectrometry; Journal of Exposure Science and Environmental Epidemiology, vol. 21, No. 4, pp. 1-21. (Year: 2011).*
Fisher Chemical. High Purity Acids Trace Elemental Analysis; downloaded from https://acros.com/myBrochure/FC_High_Purity_Acids_EEM.pdf on Oct. 29, 2018. (Year: 2012).*

(Continued)

*Primary Examiner* — Sharmila G Landau
*Assistant Examiner* — Paul C Martin
(74) *Attorney, Agent, or Firm* — Quarles & Brady LLP

(57) ABSTRACT

The present invention provides methods, compositions, kits, and devices for detecting heavy metals in dried blood (e.g., dried blood spots). For example, the present invention provides: 1) dried blood spot paper that is detectably free of heavy metals and methods of preparing such paper using organic acid; 2) dried blood extraction solutions optimized for heavy metal detection (e.g., extraction solutions containing acetic acid and/or gold); 3) methods for estimating venous blood volume from dried blood mass; and 4) kits and kit components optimized for heavy metal detection in dried blood (e.g., kits with paper detectably free of heavy metals, heavy metal free skin wipes, metal free collection case, etc.).

13 Claims, 9 Drawing Sheets

(56) References Cited

OTHER PUBLICATIONS

Scribner et al. Development of Standards for Analytical Papers; U.S. Department of Commerce, National Bureau of Standards, Research Paper RP1809, vol. 39, pp. 21-27. (Year: 1947).*
Matoug et al. Study of Metals Contamination in Different Filter Papers; IOSR Journal of Environmental Science, Toxicology and Food TEchnology; vol. 3, No. 5, pp. 59-61. (Year: 2013).*
International Search Report for PCT/US2014/028146 dated Jul. 29, 2014.
Written Opinion for PCT/US2014/028146 dated Jul. 29, 2014.
International Preliminary Report on Patentability for PCT/US2014/028146 dated Jul. 29, 2014.
Laan. Area and vol. of Blood Drops: Using Optical Coherence Tomography to Determine the vol. of Bloodstains. Masters Thesis. Jan. 10, 2011.
Chaudhuri, SN., et al., "Pilot Study for utilization of Dried Blood Spots for Screening of Lead, Mercury and Cadmium in Newborns", J. Expo Sci Environ Epidemiol, 2009, 19(3): 298-316. doi: 10.1038/jesee.2008.19. Epub Apr. 9, 2008.
Mei et al., Use of Filter Paper for the Collection and Analysis of Human Whole Blood Specimens; American Society for Nutritional Sciences, 2001, 1631S-1363S (6 pages).

* cited by examiner

TREATED DRIED BLOOD SAMPLE PAPER FOR DETECTION OF HEAVY METALS IN DRIED BLOOD

CROSS REFERENCE TO RELATED APPLICATIONS

The present application is the U.S. National Stage of International Application No. PCT/US2014/028146, filed on Mar. 14, 2014, which International Application claims the benefit of priority to U.S. Provisional Patent Application 61/803,674, filed on Mar. 20, 2013, which is incorporated by reference in its entirety.

STATEMENT REGARDING FEDERAL FUNDING

This invention was made with government support under grant number HHSN267200700027C awarded by the National Institutes of Health. The government has certain rights in the invention.

FIELD OF THE INVENTION

The present invention provides methods, compositions, kits, and devices for detecting heavy metals in dried blood (e.g., dried blood spots). For example, the present invention provides: 1) dried blood spot paper that is detectably free of heavy metals and methods of preparing such paper using organic acid; 2) dried blood extraction solutions optimized for heavy metal detection (e.g., extraction solutions containing acetic acid and/or gold); 3) methods for estimating venous blood volume from dried blood mass; and 4) kits and kit components optimized for heavy metal detection in dried blood (e.g., kits with paper detectably free of heavy metals, heavy metal free skin wipes, metal free collection case, etc.).

BACKGROUND

Heavy metals, including arsenic (As), lead (Pb), mercury (Hg), and cadmium (Cd), are ubiquitous environmental toxicants. In fact, As, Pb, Hg, and Cd are listed as the $1^{st}$, $2^{nd}$, $3^{rd}$, and $7^{th}$ most important hazardous substances on the 2011 CERCLA priority list of 275 substances, respectively. Exposure to heavy metals can occur through a variety of exposure routes, including inhalation as dust and fumes, and ingestion from food and water, and can cause a wide spectrum of health problems including convulsions, coma, renal failure, injuries to the lungs and neurologic system, memory loss, delirium, diabetes, kidney damage, and a variety of cancers. Heavy metals can be quantified in blood to estimate environmental exposures. However, the requirement for venous blood, which is costly, invasive, and must be collected by a trained phlebotomist, is an obstacle for assessing heavy metal exposures. This is especially the case with pediatric populations and younger children, for whom the developmental consequences of heavy metal exposure can be particularly severe.

SUMMARY OF THE INVENTION

The present invention provides methods, compositions, kits, and devices for detecting heavy metals in dried blood (e.g., dried blood spots). For example, the present invention provides: 1) dried blood spot paper that is detectably free of heavy metals and methods of preparing such paper using organic acid; 2) dried blood extraction solutions optimized for heavy metal detection (e.g., extraction solutions containing acetic acid and/or gold); 3) methods for estimating venous blood volume from dried blood mass; and 4) kits and kit components optimized for heavy metal detection in dried blood (e.g., kits with paper detectably free of heavy metals, heavy metal free skin wipes, metal free collection case, etc.).

In some embodiments, the present invention provides kits and systems for detecting heavy metals in dried blood (e.g., dried blood spots) comprising: a) a first component comprising dried blood sample paper that is free of detectable levels of heavy metals; b) at least one second component selected from the group consisting of: i) a skin cleansing wipe this is free of detectable levels of the heavy metals; ii) a plastic collection case configured to hold the paper, wherein the plastic collection case is free of detectable levels of the heavy metals; iii) a desiccant configured to fit inside the plastic collection case; iv) a plastic ring configured to fit inside the plastic case on top of the paper and to help prevent accidental contamination of the paper, wherein the plastic ring is free of detectable levels of the heavy metals; v) a plastic support structure configured to provide a spacer between the paper and the desiccant inside the plastic collection device, wherein the plastic support structure is free of detectable levels of the heavy metals (see, e.g., plastic support in FIGS. 7-9 designed to hold the filter paper); vi) a lancing device configured to pierce human skin; and vii) a dried blood sample extraction solution comprising acetic acid and/or gold. In certain embodiments, the plastic support structure facilitates drying of the filter paper and/or it prevents contamination of the paper, before and after collection, by preventing the paper from touching any surfaces (e.g., including the box it is contained in). In some embodiments, the plastic support structure comprises a plurality of lower and upper prongs attached to a base member (e.g., as shown in FIGS. 7-9).

In certain embodiments, the dried blood sample paper is organic acid-treated paper. In further embodiments, the detectable levels are as measured by mass spectrometry (i.e., the components do not have detectable heavy metals as measured by mass spectrometry). In particular embodiments, the heavy metals include arsenic, lead, mercury, and cadmium. In other embodiments, the skin cleansing wipe comprises a pad and an alcohol (isopropanol). In further embodiments, the desiccant is configured to fit inside the plastic case below the dried blood sample paper. In particular embodiments, the lancing device comprises a disposable finger lancet.

In some embodiments, the present invention provides articles comprising dried blood sample paper that is free of detectable levels of heavy metals. In certain embodiments, the dried blood sample paper is organic acid-treated paper.

In particular embodiments, the present invention provides methods for making treated dried blood sample paper comprising: a) providing un-treated dried blood sample paper which contains detectable levels of heavy metals; and b) treating the un-treated dried blood sample paper with an organic acid under conditions such that treated dried blood sample paper is generated, wherein the treated dried blood sample paper is free of detectable levels of heavy metals.

In particular embodiments, the treating comprises submerging the un-treated dried blood sample paper into the organic acid. In further embodiments, the treating further comprises agitating the un-treated dried blood sample paper as it is submerged in the organic acid. In other embodiments, the treating further comprises rinsing the un-treated dried blood sample paper with deionized water. In additional embodiments, the organic acid is an ultratrace metals grade acid. In further embodiments, the organic acid is hydrochloric acid or nitric acid. In some embodiments, the detectable levels are as measured by mass spectrometry. In particular embodiments, the heavy metals include arsenic, lead, mercury, and cadmium.

In some embodiments, the present invention provides compositions comprising a dried blood sample extraction solution for heavy metal testing comprising: a) an organic acid; b) a surfactant; c) water; and d) acetic acid and/or gold particles.

In particular embodiments, the present invention provides methods of extracting a dried blood sample from paper comprising: treating paper comprising a dried blood sample with the dried blood sample extraction solution described above in order to generate an aqueous blood sample.

In further embodiments, the present invention provides methods for estimating venous blood volume from a dried blood spot comprising: a) weighing paper comprising a dried blood spot and subtracting the weight of the paper prior to application of the dried blood spot thereby determining the mass of the dried blood spot; and b) estimating the venous blood volume used to generate the dried blood spot by correlating the mass of the dried blood spot to the estimated venous blood volume using the slope in FIG. 4 or a slope similar to that in FIG. 4.

DETAILED DESCRIPTION

Figure 1:
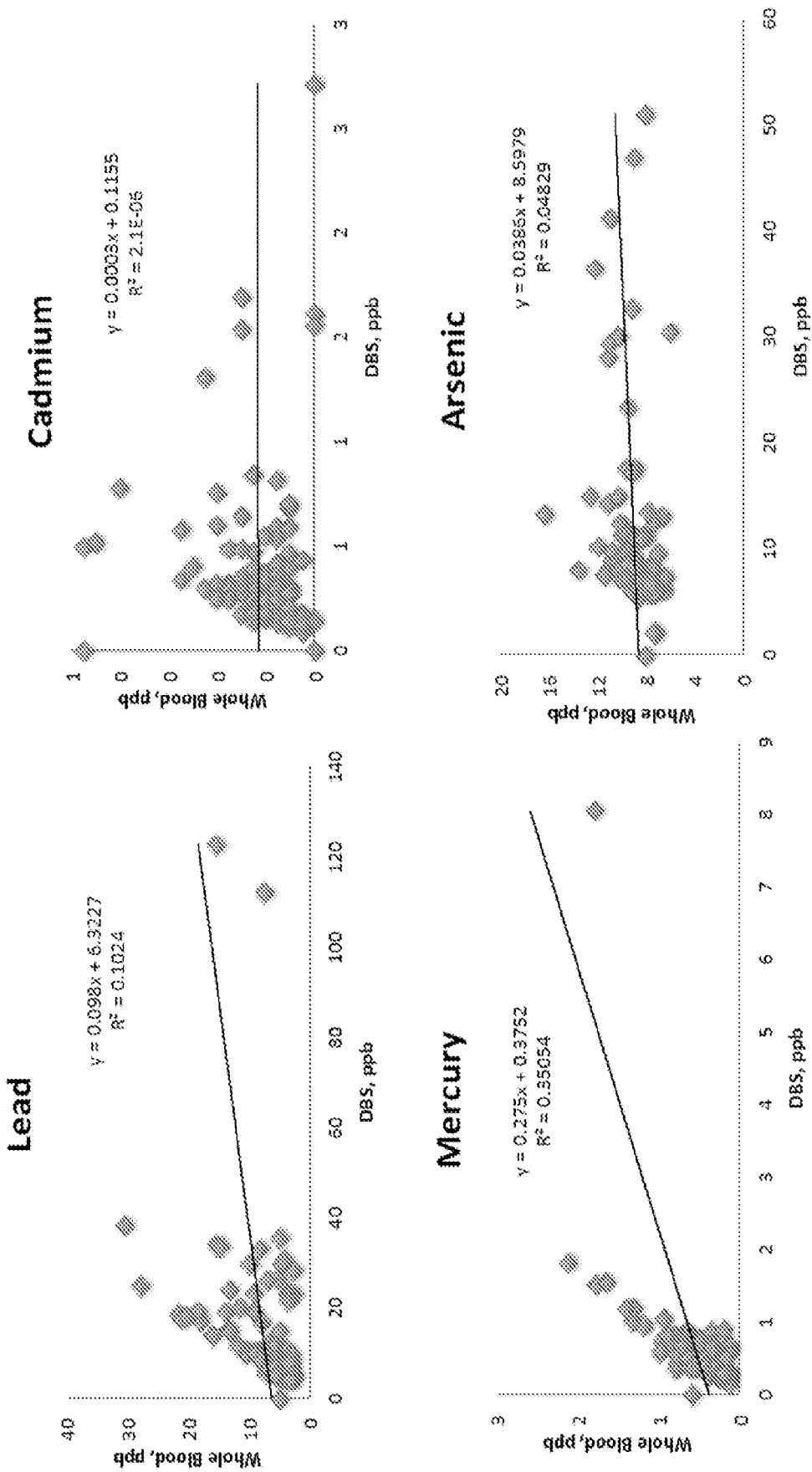
FIG. 1 shows a scatterplot and regression analysis from Example 1 below of the association between heavy metal concentrations obtained from matched venous whole blood and finger stick DBS samples for n=85 children.

The present invention provides methods, compositions, kits, and devices for detecting heavy metals in dried blood (e.g., dried blood spots). For example, the present invention provides: 1) dried blood spot paper that is detectably free of heavy metals and methods of preparing such paper using organic acid; 2) dried blood extraction solutions optimized for heavy metal detection (e.g., extraction solutions containing acetic acid and/or gold); 3) methods for estimating venous blood volume from dried blood mass; and 4) kits and kit components optimized for heavy metal detection in dried blood (e.g., kits with paper detectably free of heavy metals, heavy metal free skin wipes, metal free collection case, etc.).

Environmental exposures to heavy metals are a large concern globally, and have been a focus of many population based surveys. Currently the "gold standard" for quantifying heavy metals in blood is to use whole blood collected by venipuncture. Because venous blood collection is costly, invasive, and must be performed by a trained phlebotomist, these obstacles have been a challenge for assessing exposure to toxic metals in non-clinical settings. In addition, heavy metals (e.g. Pb) are routinely measured in clinical settings, often as part of state mandated screening programs, in younger children to assess environmental exposures. Given the draw backs of venipuncture based methods, the dried blood sample approach of the present invention provides a simple and minimally invasive methods (e.g., based on finger prick) that has large advantages for both population based surveys, public health surveillance, and standard clinical testing.

The most common filter paper used to collect dried blood spot (DBS) samples is WHATMAN® #903 Protein Saver Cards. However, while WHATMAN® #903 filter paper has been rigorously tested and optimized for measuring a variety of biomarkers, they are not designed for trace level heavy metals analysis. As a result, background contamination in the filter paper interferes with quantification of heavy metals in DBS samples and can lead to imprecise estimates of exposure.

An additional challenge for quantifying biomarkers in DBS samples is the unknown volume of blood in each sample. DBS are generally collected via a simple finger or heel stick, and as a result, the volume of blood applied to the filter paper is unknown. The common convention for determining blood volume is to take a standard punch from the blood spot (typically 3-6 mm in diameter) and estimating the blood volume based on the size of the punch. However, these crude approximations result in too much measurement error for the precise quantification of heavy metals, which are present in very small quantities.

The present invention provides methods, devices, kits, and compositions to overcome the problems in the art. In certain embodiments, the present invention provides DBS specimen collection devices that are optimized for quantification of trace level heavy metals. Examples of the innovations provided by the present invention including the following: 1) methods for pretreating the filter paper matrix to remove heavy metal contamination prior to blood collection; 2) an algorithm for determining blood volume, based on the mass of the blood collection device before and after blood collection; 3) a blood collection device in which the pretreated filter paper is secured to a metal-free plastic (e.g., polypropylene) ring to protect the blood collection surface from contacting surfaces that may contaminate the blood sample; 4) a blood collection device that is contained inside a metal-free plastic (e.g., polypropylene) case to avoid contamination before, during, and after blood collection; 5) the use of a desiccant in the plastic case, preferably positioned beneath a metal-free plastic grid, to absorb water as the sample is dried within the protective encasement; 6) use of a metal-free alcohol wipe pad for cleaning the skin (e.g., finger) prior to blood collection, to eliminate contamination from the finger (and to reduce risk of infection at the site of puncture); and 7) points 4 and 6 above facilitating the shipment of samples without concerns about stability or contamination, and allow for the collection of samples in home, community, and clinic based settings (which is not the case with venipuncture-based collection methods).

Figure 7:
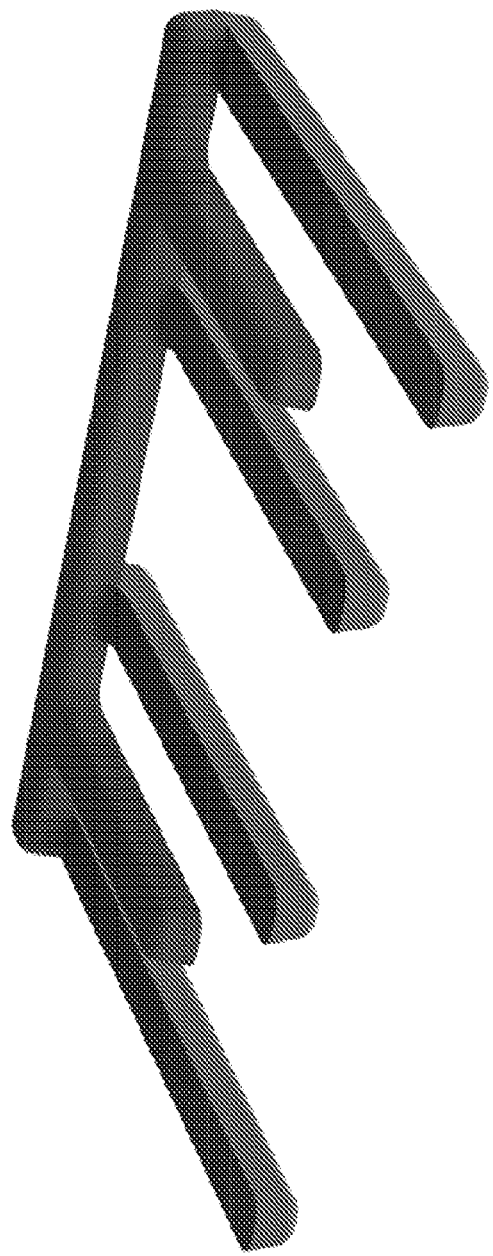
FIG. 7 shows an exemplary plastic support configured to hold filter paper (e.g., and to provide a spacer between the paper and desiccant inside the collection case). The exemplary plastic support in FIG. 7 has two upper prongs and four lower prongs attached to a base rod and is free of detectable levels of heavy metals. In certain embodiments, different numbers of upper and lower prongs are employed (e.g., three-six lower prongs and five-eight upper prongs, etc.).
Figure 8:
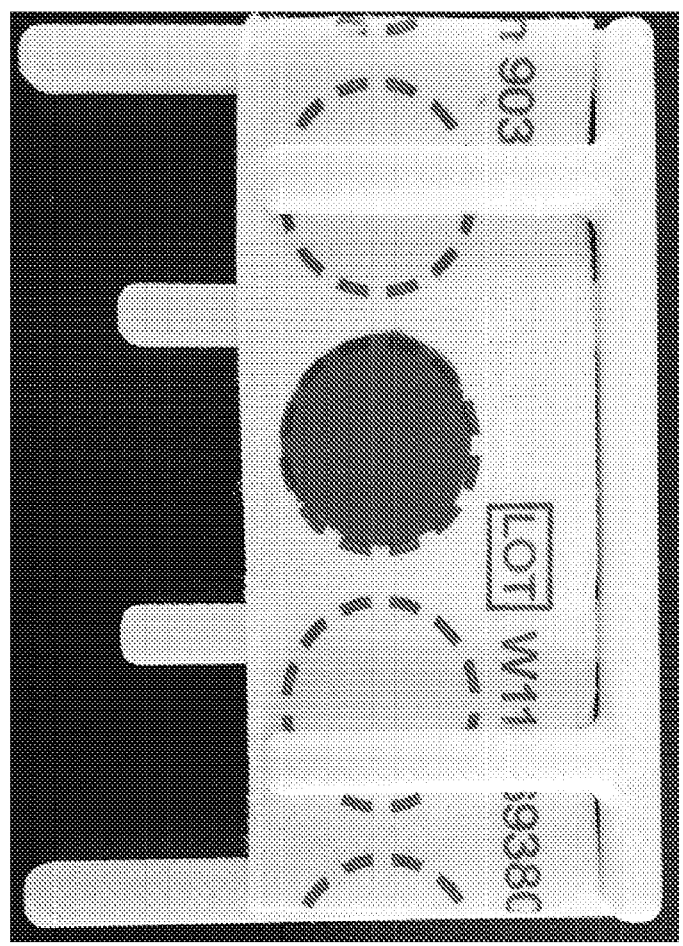
FIG. 8 shows the same type of exemplary plastic support as in FIG. 7, but includes filter paper inserted therein, wherein the filter paper contains a dried blood spot.
Figure 9:
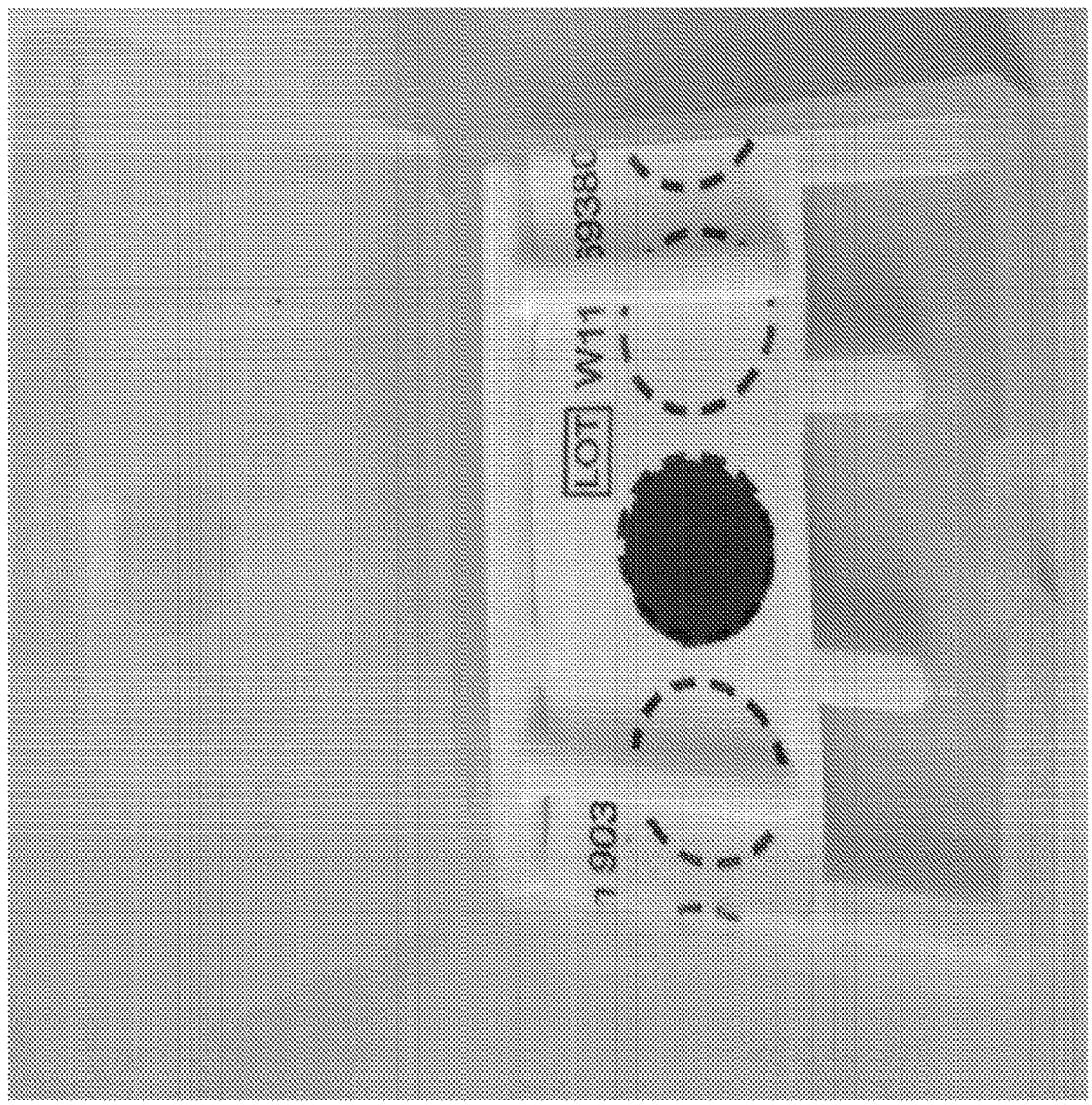
FIG. 9 shows the same type of exemplary plastic support as in FIG. 8 with inserted filter paper, where the support and paper are located in a plastic case. The plastic case may, in some embodiments, have a desiccant located therein.

The present invention provides kits. The kits of the present invention can have at least one or more of the following components: a) free or detectably heavy metal free DBS paper; b) free or detectably heavy metal free wipes; c) free or detectably metal free collection case composed of plastic; d) desiccant configured to be inside the collection case (e.g., below blood collection paper); e) plastic DBS ring (e.g., that prevents accidental contamination of paper surface); f) plastic grid or other structure configured to be inserted in collection case under paper (or holding the paper, as shown in FIGS. 7-9), on top of desiccant; g) lancets (sterile disposable finger lancets); and i) an extraction solution containing acetic acid and/or gold.

Figure 6:
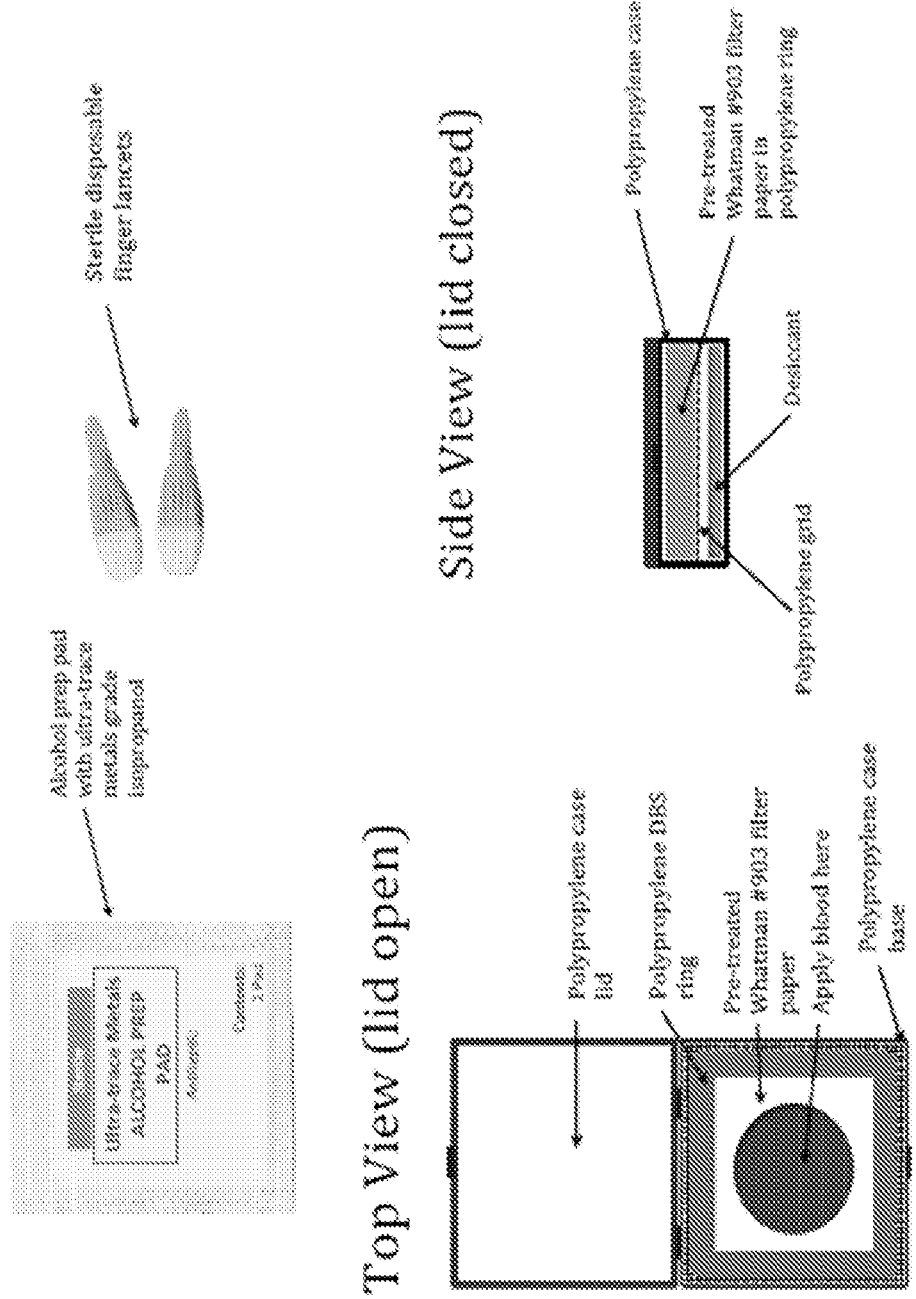
FIG. 6 shows the components for an exemplary heavy metal DBS test kit.

An exemplary kit is shown in FIG. 6. As shown in this figure, this exemplary kits has: an alcohol prep pad with ultra-trace metals grade isopropanol; two sterile disposable finger lancets; a polypropylene collection case (composed of lid and base); a polypropylene DBS ring on top of the paper; pre-treat detectably heavy metal free blood spot paper (e.g., WHATMAN® #903 paper); a polypropylene support grid underneath paper; and a desiccant below the support grid.

As described in Example 1 below, this Example reports a method to quantify heavy metals in DBS that performs at a level that is comparable to venous whole blood-based methods. This simple, and non-invasive blood collection method provides an alternative means of obtaining blood specimens for assessing exposures to toxic metals using a single drop of blood (e.g., collected from a finger or heel prick). Example 1 provides methods to estimate the volume of blood used in a assay for quantifying heavy metals using dried blood mass. The mass of the blood collection device is determined before and after blood collection, strictly controlling temperature and humidity. Initial results show that dried blood mass is highly associated with venous blood volume.

In certain embodiments, the present invention employs metal-free alcohol wipes (e.g., non-detectable metal in the wipes as measured by conventional, non-extreme methods). Metal contamination from the site of blood collection, and contamination from standard grade isopropanol used in alcohol pads, are potential sources of contamination. In certain embodiments, the wipes are part of a DBS collection kit, and are composed of metal free pads and ultra-trace metals grade isopropanol (or other alcohol) absorbed onto metal-free pads. In certain embodiments, a desiccant is included in the metal free collection case near the blood collection paper. In particular embodiments, a desiccant is sealed inside the metal-free case beneath the blood collection paper to absorb water during the blood drying process. The desiccant may be separated from the sample using a metal-free plastic support (e.g., polypropylene grid). In certain embodiments, during blood collection, the lid on the collection case will be opened briefly during blood collection and then immediately sealed following blood application to the paper (or other blood collection device) to avoid contamination. In certain embodiments, the kits and devices of the present invention are collected outside the clinic (e.g., home, in the field, etc.) and are shipped to a lab (e.g., at room temperature) in an envelope (e.g., flat envelope).

EXAMPLE

Example 1

Heavy Metal Detection in Dried Blood Spots

This example describes heavy metal detection in dried blood spots and specifically describes a targeted extraction and analytical procedure optimized for specifically quantifying As, Pb, Hg, and Cd in DBS specimens. Major features of this protocol include: 1) the use of a one-batch extraction procedure to avoid contamination and analyte loss during transfer and filtration steps, 2) the addition of gold (Au) in the extraction solution to amalgamate Hg and enhance recovery and prevent loss of Hg throughout the analytical procedure, 3) normalization of dried blood mass to more precisely estimate relative blood volumes, 4) the use of paired filter paper blanks for all DBS samples to evaluate background contamination in the WHATMAN® #903 Protein Saver cards, and 5) use of an organic acid (ultra-trace metals grade acetic acid) to enhance the signal for As.

All samples were excised using ceramic scissors (VWR, Atlanta, Ga.) that were acid washed in a 5% acetic acid (v/v) solution overnight prior to use, and samples were handled with acetic acid washed TEFLON® polytetrafluoroethylene tweezers. Entire DBS specimens were excised using the printed guidelines on the blood collection cards as a guide. The volume of blood in an intact DBS is approximately 60 µl. However, to account for blood volume variation between samples, the dried mass of each sample was normalized to the mean mass of all of the excised samples. A similar approximate size of a blank filter paper is excised from each card near each blood sample to account for background metal contamination in the filter paper. The mass of each blank was also normalized to the mean mass of all of the excised blanks. DBS and filter paper blanks were weighed in 15 ml metal-free polypropylene centrifuge tubes (VWR, Atlanta, Ga.). An extraction solution was prepared using 5% ultrapure grade acetic acid and 0.01% ultrapure grade Triton X-100 (Fisher Scientific, Pittsburgh, Pa.) in 18.2 mΩ deionized water. Two hundred ppb of Au was added to amalgamate Hg and prevent analyte loss throughout the procedure (Inorganic Ventures, Christiansburg, Va.). One and a half ml of extraction solution was added directly to each vial. Five ppb of indium, bismuth, and yittrium were added to the extraction solution as internal standards (Inorganic Ventures, Christiansburg, Va.). DBS samples and filter paper blanks were centrifuged at 3600×g for 2 minutes and incubated for 90 minutes at room temperature on a shaker table at 300 rpm. Prior to analysis the centrifuge tubes were inverted and manipulated to adhere the filter paper to the side of the tubes in order to remove them from the blood extracts. Filtration was avoided to prevent contamination and analyte loss.

Concentrations of As, Pb, Hg, and Cd were quantified using a ThermoFisher X Series II Inductively Couple Plasma Mass Spectrometer (ICP-MS). The instrument detection limits were determined to be in the low ppt range for each element. Metal concentrations were quantified based on a five-point calibration curve for each analyte. For Pb, three isotopes were scanned and summed (m/z: 206, 207, and 208). As, Hg, and Cd, were quantified using single isotopes with m/z of 75, 202, and 111, respectively. In addition to the samples and paired card blanks, quality control samples were run along with each batch, consisting of a matrix blank, a trace element whole blood reference (ClinChek, Munich, Germany), and a trace element whole blood reference spiked onto WHATMAN® #903 filter paper.

For method validation, 85 matched venous whole blood and finger stick DBS samples were collected at a Hospital in Illinois. Volunteers were between the ages of 1 and 21. Venous blood samples were collected in metal-free vacutainers, and DBS samples were collected using WHATMAN® #903 Protein Saver cards. DBS were dried at room temperature for four hours and placed in plastic bags with desiccant packs. All samples were frozen at −80° C. until shipped to the Northwestern Laboratory for Human Biology Research on dry ice.

Concentrations of heavy metals in matched whole blood and DBS samples are provided in FIG. 1. Correlations between whole blood and DBS samples were very low for Pb, Cd, and As. Mercury had the strongest correlation between samples with an R2=0.35. However, these results were skewed by a single outlier that contained elevated levels of Hg in the DBS sample. Concentrations of heavy metals were also quantified in pair-wise blank DBS samples (data not shown). Lead concentrations in the blank samples were significant. However, Pb contamination was determined to be non-homogenously distributed across the cards. Background contamination of Hg, Cd, and As were mostly low, but significant given the trace level concentrations of these metals that are generally found in blood. Pair-wise subtraction of the blank samples from the DBS modestly improved the correlation between Hg in the matched venous whole blood and DBS samples, increasing the R2 from 0.35 to 0.52. However, using pair-wise subtraction did not significantly improve the correlation between venous blood and DBS samples for Pb, Cd, and As, which were 0.11, 1.5× $10^{-5}$, and 0.04, respectively.

Overall, heavy metal contamination in the WHATMAN® #903 filter paper was significant, and alternative blood collection methods are required for accurately quantifying trace level heavy metals in DBS samples.

A method was developed to pretreat the WHATMAN® #903 filter paper to remove heavy metals prior to blood collection. Sections of each card containing the printed blood collection guides were excised with ceramic scissors. Three cards were placed in 1 L of 5% ultratrace metals grade hydrochloric acid and 5% ultratrace metals grade nitric acid in 18.2 mΩ deionized water (VWR BDH Aristar Ultra, Chicago, Ill.). Metal extraction was performed in Nalgene Low Metals bottles (Fisher Scientific, Pittsburgh, Pa.) at room temperature on a shaker table for 90 minutes at 300 rpm. Following metals extraction the cleaned cards were rinsed twice using 1 L of 18.2 mΩ deionized water. The extraction bottles were then filled with an additional 1 L of 18.2 mΩ deionized water and placed on a shaker table for 15 minutes at 300 rpm. The cards were then rinsed an additional two times using 1 L of 18.2 mΩ deionized water for each wash. The cleaned filter paper was then removed using acid washed TEFLON® polytetrafluoroethylene tweezers and dried overnight suspended within a fume hood.

Pretreated filter paper samples were extracted and analyzed using the method described above. For comparison, untreated WHATMAN® #903 cards were also excised and analyzed the same conditions and same amount of sample.

Figure 2:
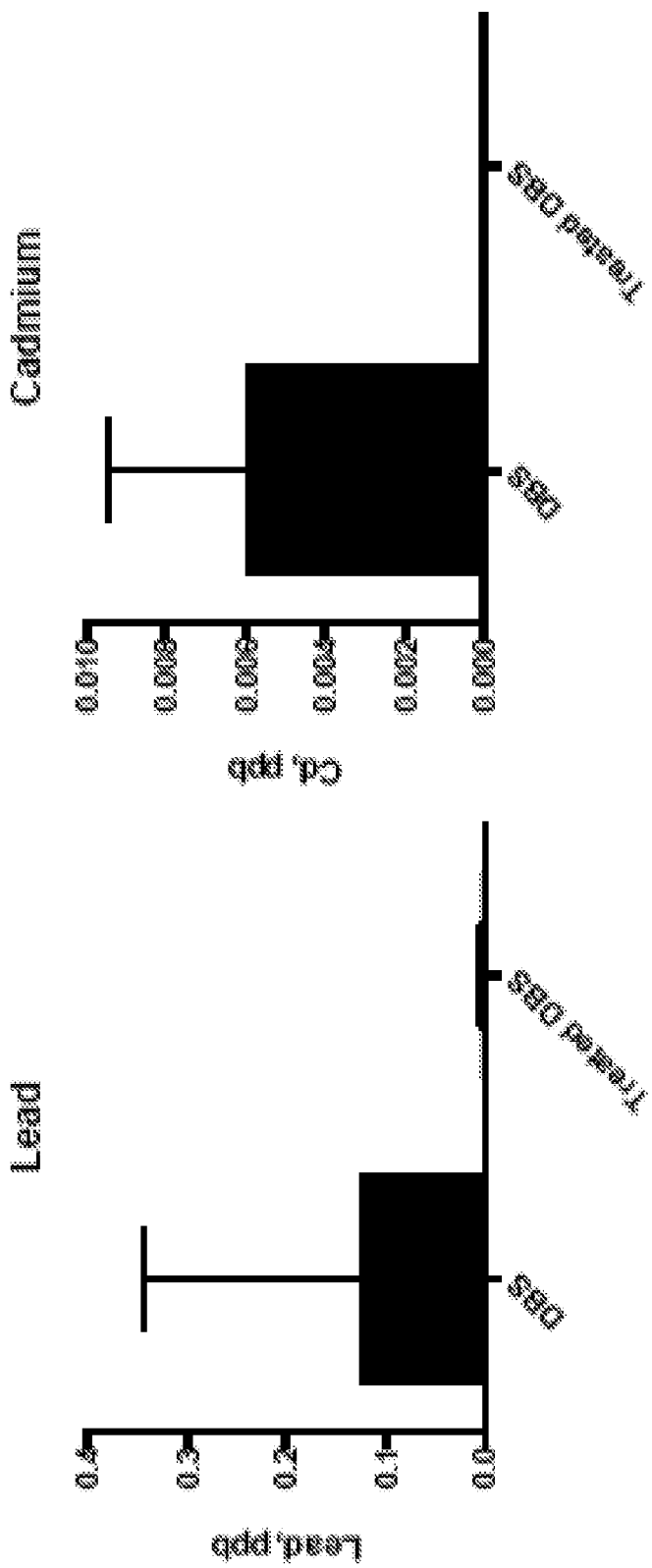
FIG. 2 shows results from Example 1 below, providing concentrations of Pb and Cd measured in treated and untreated WHATMAN® #903 filter paper. After treatment all metals were undetectable.

Concentrations of Pb, Cd, Hg, and As were below the level of detection in all pretreated samples. Differences between the treated and untreated filter paper were most significant for Pb and Cd (FIG. 2). This procedure was effective in reducing all trace levels of heavy metals below the instrument detection limit.

An experiment was performed to assess the performance of the pretreated filter paper for quantifying trace level heavy metals in blood. Whole blood samples (described above) were spotted onto cleaned filter paper in 60 μL aliquots. All DBS samples were dried overnight (n=54). Matched venous whole blood and DBS samples were analyzed for Pb, Cd, Hg, and As using the method described above.

Figure 3:
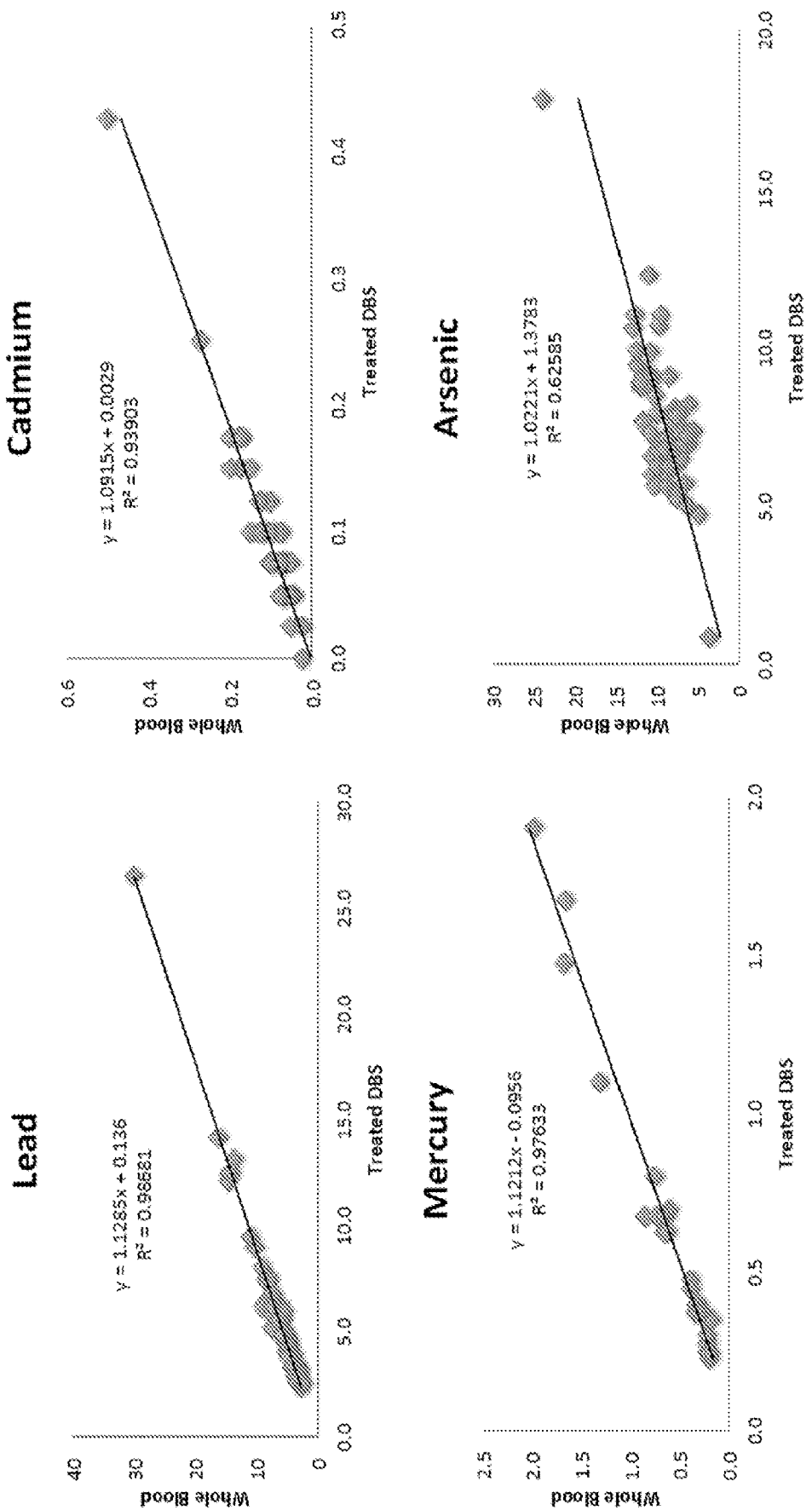
FIG. 3 shows results from Example 1 below, providing scatterplots and regression analysis of the association between heavy metals obtained from matched venous blood and DBS samples collected on pretreated WHATMAN® #903 filter paper.

Pretreatment of the WHATMAN® #903 filter paper to remove heavy metals prior to blood application did not appear to alter the blood absorbance and distribution properties of the filter paper. As with untreated cards, 60 μL of blood completely filled the printed blood collection guidelines. Scatterplots of the matched venous blood and DBS samples using pretreated filter paper are provided in FIG. 3. Quantification of heavy metals in DBS collected on pretreated WHATMAN® n #903 filter paper provided comparable precision to the venous blood "gold standard" method.

For relative comparisons of heavy metals in DBS, such as in case control studies, blood volumes can be normalized by adjusting the excised mass of a DBS to the mean mass of all of the samples within a study (using the printed guidelines on the WHATMAN® #903 paper to excise approximately the same volume from each sample). However, for population screening, absolute concentrations of heavy metals are of interest rather than relative values.

Figure 4:
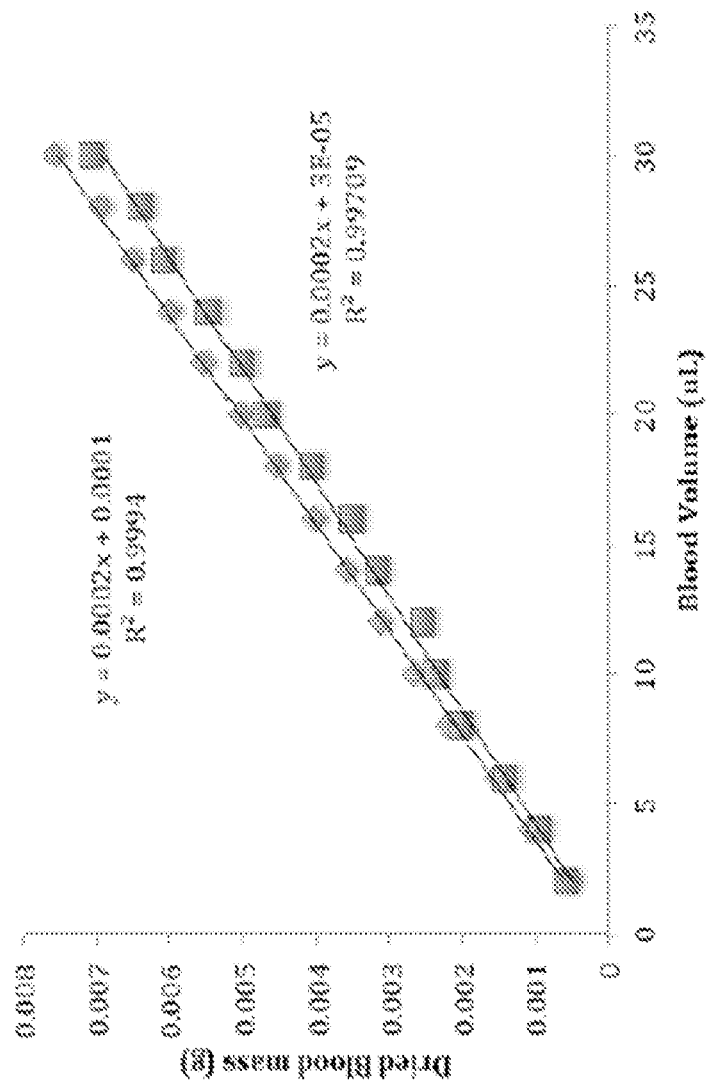
FIG. 4 shows results from Example 1, providing the association between dried blood mass and venous blood volume. Male sample points are smaller diamonds, while female sample points are larger squares.

To estimate blood volumes in DBS samples, the mass of the WHATMAN® #903 filter paper samples was determined before and after blood application. After blood was applied to the filter paper, all samples were completely dried prior to obtaining the post-blood application masses. To determine the association between dried blood mass and venous blood volume, measured concentrations of venous blood was applied to WHATMAN® #903 filter paper in volumes ranging from 2-30 μL. The results from this experiment are provided in FIG. 4. Dried blood masses and venous blood volumes were highly correlated. Minor differences were observed between males and females.

Figure 5:
FIG. 5 shows results from Example 1, providing an estimation of venous blood volume from dried blood mass.

Validation experiments were performed to determine how precisely venous blood volumes could be estimated from dried blood mass using DBS samples that were spotted with known blood volumes of blood, that were blinded to the analyst. Blood was applied at different volumes using whole blood collected from nine male and female volunteers. Blood volume estimations were calculated using averages of male and female values from FIG. 4. Results are provided in FIG. 5. These results suggest that dried blood mass can be used to accurately estimate venous blood volume.

All publications and patents mentioned in the present application are herein incorporated by reference. Various modification and variation of the described methods and compositions of the invention will be apparent to those skilled in the art without departing from the scope and spirit of the invention. Although the invention has been described in connection with specific preferred embodiments, it should be understood that the invention as claimed should not be unduly limited to such specific embodiments. Indeed, various modifications of the described modes for carrying out the invention that are obvious to those skilled in the relevant fields are intended to be within the scope of the following claims.

We claim:

1. A method for making a treated dried blood sample (DBS) paper that is free of detectable levels of arsenic (As), lead (Pb), mercury (Hg), and cadmium (Cd) of no more than parts-per-trillion (ppt) as measured by inductively coupled plasma mass spectrometry (ICP-MS), the method comprising steps of:

(a) treating a DBS paper which contains detectable levels of arsenic (As), lead (Pb), mercury (Hg), or cadmium (Cd) with an acid solution consisting of a mixture of hydrochloric acid and nitric acid in deionized water; and (b) washing the treated DBS paper with deionized water; wherein the method is performed under conditions such that the treated DBS paper is obtained that is free of detectable levels of arsenic (As), lead (Pb), mercury (Hg), and cadmium (Cd) of no more than parts-per-trillion (ppt) as measured by inductively coupled plasma mass spectrometry (ICP-MS).

2. The method of claim 1, wherein the treating step (a) comprises submerging the DBS paper into the acid solution.

3. The method of claim 2, wherein the treating step (a) further comprises agitating the DBS paper as it is submerged in the acid solution.

4. The method of claim 1, wherein the hydrochloric acid is an ultratrace metals grade hydrochloric acid.

5. The method of claim 1, wherein the nitric acid is an ultratrace metals grade nitric acid.

6. A method for making a treated dried blood sample (DBS) paper that is free of detectable levels of arsenic (As), lead (Pb), mercury (Hg), and cadmium (Cd) of no more than parts-per-trillion (ppt) as measured by inductively coupled plasma mass spectrometry (ICP-MS), the method comprising steps of:

(a) treating a DBS paper which contains detectable levels of arsenic (As), lead (Pb), mercury (Hg), or cadmium (Cd) with an acid solution consisting of a mixture of 5% hydrochloric acid and 5% nitric acid in deionized water; and (b) washing the treated DBS paper with deionized water; wherein the method is performed under conditions such that the treated DBS paper is obtained that is free of detectable levels of arsenic (As), lead (Pb), mercury (Hg), and cadmium (Cd) of no more than parts-per-trillion (ppt) as measured by inductively coupled plasma mass spectrometry (ICP-MS).

7. The method of claim 6, wherein the treating step (a) comprises submerging the DBS paper into the acid solution.

8. The method of claim 7, wherein the treating step (a) further comprises agitating the DBS paper as it is submerged in the acid solution.

9. The method of claim 6, wherein the hydrochloric acid is an ultratrace metals grade hydrochloric acid.

10. The method of claim 6, wherein the nitric acid is an ultratrace metals grade nitric acid.

11. A method for making a treated dried blood sample (DBS) paper that is free of detectable levels of arsenic (As), lead (Pb), mercury (Hg), and cadmium (Cd) of no more than parts-per-trillion (ppt) as measured by inductively coupled plasma mass spectrometry (ICP-MS) of no more than parts-per-trillion (ppt), the method consisting of steps of:

(a) treating a DBS paper which contains detectable levels of arsenic (As), lead (Pb), mercury (Hg), or cadmium (Cd) with an acid solution consisting of a mixture of hydrochloric acid and nitric acid in deionized water; and (b) washing the treated DBS paper with deionized water; wherein the method is performed under conditions such that the treated DBS paper is obtained that is free of detectable levels of arsenic (As), lead (Pb), mercury (Hg), and cadmium (Cd) of no more than parts-per-trillion (ppt) as measured by inductively coupled plasma mass spectrometry (ICP-MS).

12. The method of claim 11, wherein the hydrochloric acid is an ultratrace metals grade hydrochloric acid.

13. The method of claim 11, wherein the nitric acid is an ultratrace metals grade nitric acid.

\* \* \* \* \*